US009086527B2

(12) United States Patent
Parakka et al.

(10) Patent No.: US 9,086,527 B2
(45) Date of Patent: Jul. 21, 2015

(54) SILICONE-CONTAINING MONOMER

(71) Applicant: DSM IP Assets B.V., Heerlen (NL)

(72) Inventors: James Parakka, Echt (NL); Ananth Iyer, Echt (NL); Durgaprasad Chalasani, Echt (NL); Li Li, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/109,951

(22) Filed: Dec. 17, 2013

(65) Prior Publication Data
US 2014/0206830 A1    Jul. 24, 2014

Related U.S. Application Data

(63) Continuation of application No. PCT/EP2012/062849, filed on Jul. 3, 2012.

(60) Provisional application No. 61/503,561, filed on Jun. 30, 2011.

(51) Int. Cl.
| C07D 231/00 | (2006.01) |
| G02B 1/04 | (2006.01) |
| C08F 220/20 | (2006.01) |
| C08F 220/56 | (2006.01) |
| C08F 226/10 | (2006.01) |
| C07F 7/08 | (2006.01) |
| C08G 77/14 | (2006.01) |
| C08G 77/26 | (2006.01) |
| C08F 220/40 | (2006.01) |
| C08F 230/08 | (2006.01) |

(52) U.S. Cl.
CPC .............. *G02B 1/043* (2013.01); *C08F 220/20* (2013.01); *C08F 220/56* (2013.01); *C08F 226/10* (2013.01); *C07F 7/0812* (2013.01); *C08F 220/40* (2013.01); *C08F 230/08* (2013.01); *C08G 77/14* (2013.01); *C08G 77/26* (2013.01)

(58) Field of Classification Search
CPC ...... C07F 7/1812; C08G 77/14; C08G 77/26; G02B 1/043
See application file for complete search history.

(56) References Cited

U.S. PATENT DOCUMENTS

| 5,959,117 | A | 9/1999 | Ozark |
| 6,022,926 | A * | 2/2000 | Dietz et al. .................... 524/837 |
| 6,770,707 | B2 * | 8/2004 | Henry et al. .................. 524/588 |
| 2008/0003438 | A1 * | 1/2008 | Worley et al. ................. 428/447 |
| 2010/0331318 | A1 | 12/2010 | Hubschwerlen |

OTHER PUBLICATIONS

Demaray, Jeffrey A. et al., "Synthesis of triazole-oxazolidinones via a one-pot reaction and evaluation of their antimicrobial activity," Bioorganic & Medicinal Chemistry Letters, 18(17) 2008, 4870-4870.
Madar, D. J. et al., "Synthesis of N-arylated oxazolidinones via a palladium catalyzed cross coupling reaction. Application to the synthesis of the antibacterial agent Dup-721," Tetrahedron Letters, 42(22) 2001, 3681-3684.
Lipshutz, Bruce H. et al., "Microwave-assisted heterogeneous cross-coupling reactions catalyzed by nickel-incharcoal (Ni/C)," Chemistry—An Asian Journal, 1(3) 2006, 421-421.
European Patent Office, International Search Report, PCT/EP2012/062849, Nov. 13, 2012, 1-3.

* cited by examiner

*Primary Examiner* — Margaret Moore
(74) *Attorney, Agent, or Firm* — Jeffrey R. Ramberg

(57) ABSTRACT

Silicone-containing monomer of formula (I);

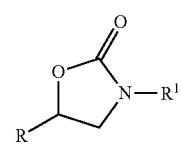

wherein said silicone-containing monomer comprises a silicone-containing moiety and an oxazolidinone moiety and wherein R is a silicone-containing moiety, and $R^1$ may be an H,

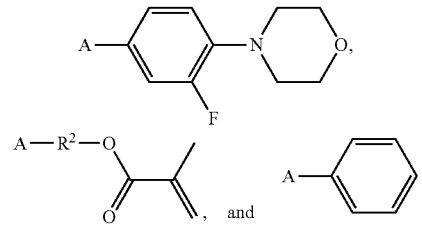

wherein A represents the oxazolidinone ring of the oxazolidinone moiety and $R^2$ is a divalent $C_{1-25}$ alkylene or $C_{6-30}$ arylalkylene. The monomer is used for the preparation of a composition for use in manufacturing of ophthalmic lenses potentially with anti-infective properties. Also, methods of making the present monomers are described.

15 Claims, No Drawings

SILICONE-CONTAINING MONOMER

BACKGROUND OF THE INVENTION

Silicone hydrogels have been the material of choice for a variety of applications including ophthalmic devices, wound dressing material, and as a drug release medium. Compatibilizing of hydrophilic and hydrophobic components within silicone hydrogel formulations is critical far the manufacturing of optically clear wettable contact lenses.

While patient comfort has driven the market use of contact lenses, the modality for use of these lenses depends on both the physical properties (including oxygen transport and lubricity of the lens) as well as the amount of protein and lipid deposition on the lenses during wear. In a silicone hydrogel contact lens the oxygen transport property which has been correlated to lens comfort can be successfully accessed by using designed silicone compounds while the wettability can be achieved by different methods of incorporation of hydrophilic components. Different technologies exist today to present a final lens that has the optical clarity and the desired wettability and lubricity, with controllable modulus and high oxygen transmissibility in the silicone hydrogel lenses.

Adsorption of unwanted components from the ocular tear fluid on to the lens material during wear is one of the contributory factors for causing reduced comfort experienced by patients. In addition, bacterial infections can potentially occur if lens care regimens are not followed for use of the lenses. The extent of undesirable adsorptions on the lens will determine the lens care needs for a specific lens and will impact on the duration the contact lens can be present in the eye.

Infection as a result of contact lens wear for prolonged periods of time partly due to improper use of lens care solution is not uncommon. While contact lens manufacturers have resorted to daily disposable lenses to limit this phenomenon, in order to minimize infection due to contact lens wear, drug release and/or release of antimicrobial components during contact lens wear is an attractive approach.

FIELD OF THE INVENTION

The present invention is directed to silicone-containing monomers comprising a silicone-containing moiety and an oxazolidinone moiety for the preparation of medical devices, or more specifically, silicone hydrogel (SiHy) ophthalmic device compositions for use in manufacturing of contact lenses. In addition, the silicone-containing monomers may be used as a compatibilizing component with anti-infective properties in a silicone hydrogel contact lens formulation. Finally, the present monomers may be used to generate surfaces having antimicrobial properties. The present disclosure also describes methods of making the present monomers, and their uses.

DESCRIPTION OF RELATED ART

Silicone hydrogels have been the material of choice for ophthalmic devices, wound dressing material and as drug release mediums. In the ophthalmic device arena, the manipulation of silicone hydrogels has improved clarity and wettability of the resultant contact lenses. However, infection is a common result of the extended wear of contact lenses. One solution provided by contact lens manufacturers is to generate daily use contact lenses.

Another approach would be to have antimicrobial contact lenses. Recent reports have investigated use of silver based compositions to provide effective antimicrobial function in the lenses. [See U.S. 2008/0102122 A1] However, the materials described to generate anti-microbial lenses by incorporating silver based materials have the tendency to cause leaching of the silver ions leading to potential toxicity concerns. Furthermore, silver is known to darken upon exposure to light. This can lead to discoloration of a lens, and possible effects on lens clarity.

The incorporation of anti-microbial drugs into contact lenses also has drawbacks. Quaternary silane (Quat) based or ion based antimicrobial materials [US2007/0242215 A1 and US2008/0004414 A1] have the potential drawback of causing undesired protein adsorption resulting in patient discomfort and complications resulting from ocular infections.

The use of halide containing oxazolidinones has been reported in literature [see US 2007/0155852]. In this patent publication the oxazolidinone structures that are disclosed are structurally different and the halide substituents in the oxazolidinone moiety are claimed for presenting the antimicrobial properties.

The current invention discloses silicone-containing monomers bearing an oxazolidinone moiety, which function as an effective compatibilizer, for both hydrophilic and hydrophobic components of a lens formulation and generate wettable lenses that have potential antibacterial properties for preventing and treating ocular infections.

BRIEF SUMMARY OF THE INVENTION

The present invention is directed to silicone-containing monomers. These silicone-containing monomers may be silicone-containing monomers comprising oxazolidinone moieties. The inventive monomers may be used in the preparation of silicone hydrogel compositions for use in the manufacturing of ophthalmic devices. The silicone reactive monomers of the invention find utility as effective compatibilizers for both hydrophilic and hydrophobic components of a contact lens formulation and may have anti-infective properties, as a result of the presence of oxazolidinone groups, and by the addition of other anti-microbial groups or atoms. The present invention also includes methods of making the present monomers.

The monomers of the present invention can be used for reactive surface wettable, lubricating functions, and may also be anti-infective. They can be used in devices such as contact lenses.

The present invention, in one embodiment, relates to a silicone-containing monomer of formula (I);

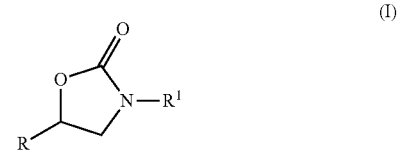

wherein said silicone-containing monomer comprises a silicone-containing moiety and an oxazolidinone moiety and wherein R is a silicone-containing moiety, and $R^1$ may be an H,

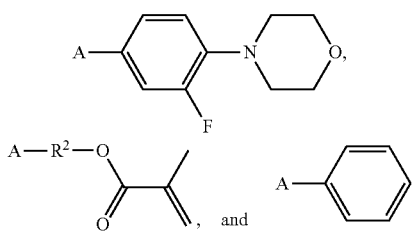, and 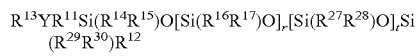

wherein A represents the oxazolidinone ring of the oxazolidinone moiety and $R^2$ is a divalent $C_{1-25}$ alkylene or a $C_{6-30}$ arylalkylene radical.

In one embodiment of the of the invention, the silicone-containing moiety R has the formula:

$$R^{13}YR^{11}Si(R^{14}R^{15})O[Si(R^{16}R^{17})O]_r[Si(R^{27}R^{28})O]_tSi(R^{29}R^{30})R^{12}$$

in which:
$R^{14}$, $R^{15}$, $R^{16}$, $R^{17}$, $R^{27}$, $R^{28}$, $R^{29}$, and $R^{30}$, independently of one another, are $C_{1-6}$ alkyl, $C_{1-4}$ alkyl-substituted phenyl, $C_{1-4}$ alkoxy-substituted phenyl, fluoro($C_{1-16}$ alkyl), cyano($C_{1-12}$ alkyl), hydroxy-$C_{1-6}$ alkyl, amino-$C_{1-6}$ alkyl;
Y denotes —COO—, —CONR$^{15}$—, —OCCO—, or —OCONR$^{18}$—, where each $R^{18}$ is independently H or $C_{1-7}$ alkyl;
$R^{11}$ denotes a divalent $C_{1-25}$ alkylene or $C_{6-30}$ arylalkylene radical, which may interrupted by —O—, —COO—, —CONR$^{16}$—, —OCOO— or —OCONR$^{18}$— and may comprise a hydroxy group, a primary, secondary, or tertiary amine group, a carboxy group, or carboxylic acid;
$R^{12}$ is a monovalent $C_{1-25}$ alkyl or $C_{6-30}$ aryl radical, which may interrupted by —O—, —COO—, —CONR$^{14}$—, —OCOO— or —OCONR$^{14}$— and may comprise a hydroxy group, a primary, secondary, or tertiary amine group, or a carboxy group;
$R^{12}$ is a monovalent $C_{1-25}$ alkyl or $C_{6-30}$ aryl radical, which comprises at least one hydroxy group, primary or secondary amine group, carboxy group, or site of olefinic unsaturation; and r and t independently of each other are an integer of up to 700 and (r+t) is from 1 to 700.

In another embodiment, the silicone containing moiety R has the formula

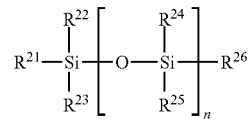

$R^{21}$ denotes a divalent $C_{1-25}$ alkylene or $C_{6-30}$ arylalkylene radical, which may interrupted by —O—, —COO—, —CONR$^{18}$—, —OCOO— or —OCONR$^{18}$— and may comprise a hydroxy group, a primary, secondary, or tertiary amine group, a carboxy group, or carboxylic acid;

$R^{26}$ is a monovalent $C_{1-25}$ alkyl or $C_{6-30}$ aryl radical, which comprises at least one hydroxy group, primary or secondary amine group, carboxy group, or site of olefinic unsaturation;

$R^{22}$ through $R^{25}$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group, and wherein n ranges from 1-700, In a further embodiment of the composition, the silicone-containing monomer is selected from the group consisting of:

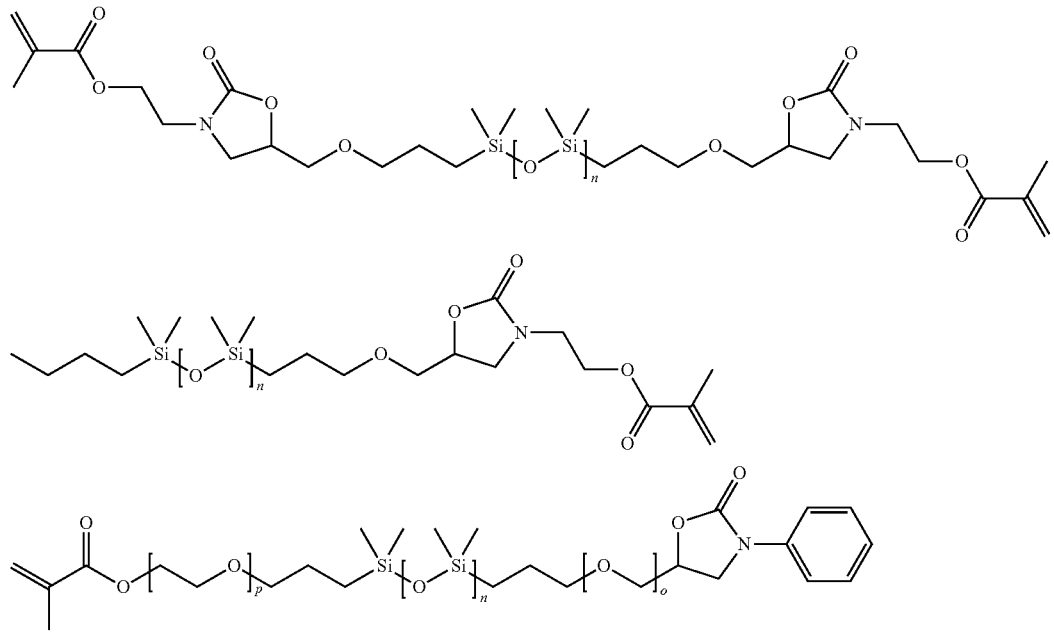

-continued

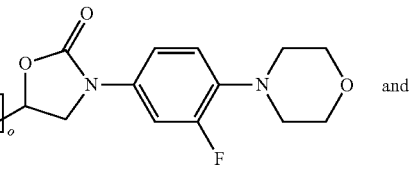
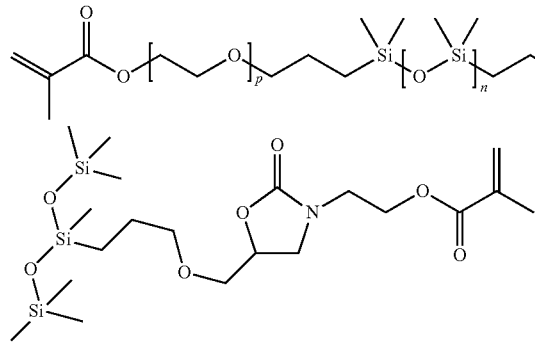

wherein n is an integer ranging from 1-700, o is an integer ranging from 0 to 1, and p is an integer ranging from 0-50.

In a further embodiment of the invention relates to a composition comprising a silicone-containing monomer as described above and at least one other monomer.

The composition preferably comprises 1-90 wt % based on the total weight of the composition of a silicone-containing monomer; more preferably 1-50 wt %, most preferably 10-50 wt %.

The composition preferably comprises 10-99 wt % based on the total weight of the composition of a feast one other monomer, more preferably 50-99 wt %, most preferably 50-90 wt %.

In a further embodiment the composition comprises a silver salt, bromine or iodine.

In another embodiment the composition comprises an initiator and the composition is thermally cured, or cured by ultra-violet (UV) radiation.

In a further embodiment, the composition comprises a silver salt, bromine, or iodine.

A further embodiment of the invention relates to a medical device comprised of the cured composition of the invention, such as an ophthalmic device, including but not limited to a contact lens.

The invention further relates to a process for the preparation of a silicone-containing monomer of formula (I) comprising providing an oxirane-functionalized silicone-containing moiety R and react this oxirane-functionalized silicone-containing moiety R with an Isocyanate-functionalized group $R^1$.

Preferably, the isocyanate-functionalized compound $R^1$ also comprises a (meth)acrylate group.

DETAILED DESCRIPTION OF THE INVENTION

Unless specifically defined otherwise, the following terms have the meanings set forth below.

As used herein, the term "ophthalmic device" includes devices that reside in, on or in front of the eye, such as lenses and related devices. The lenses can provide optical correction or may be cosmetic. The term lens includes, but is not limited to soft contact lenses, hard contact lenses, intraocular lenses, overlay lenses, ocular inserts, optical inserts, spectacle lenses, goggles, surgical glasses and the like. In a preferred embodiment the ophthalmic device is a contact lens and more preferably a soft contact lens. Soft contact lenses are made from hydrogels and silicone elastomers or hydrogels, which include but are not limited to silicone hydrogels and fluoro-hydrogels. These hydrogels contain hydrophobic and/or hydrophilic monomers that are covalently bound to one another in the cured lens. Preferably, a contact lens is a clear lens.

Compatibility is intended to mean that the compatibility of the hydrophobic silicon-containing compounds with the hydrophilic compounds to result in a composition that is wettable and lubricious and is effective as an ophthalmic device or contact lens. A compatibilizer is a feature of a compound or composition which links or joins the hydrophobic and hydrophilic portions of a composition, enabling significant "wettability" and lubricity of a silicone-containing polymer.

Anti-microbial, anti-biotic and anti-infective are intended to mean reducing the growth of, preventing the growth of, or Inhibiting the growth of microbes, bacteria, other infective proteins or viruses. Anti-microbial may also include an inhibition of a reaction to toxic or inflammatory particles, proteins, or compounds. Such bacteria or other microbes include but are not limited to those organisms found in the eye, particularly *Pseudomonas aeruginosa, Acanthamoeba* species, *Staphylococcus aureus, E. Coli, Staphylococcus epidermidis*, and *Serratia marcesens*, in particular, anti-biotic or anti-microbial can refer to the prevention, inhibition, or reduction of the growth of Gram-positive bacteria or bactericidal activity. The present compositions may reduce or inhibit microbial activity by at least 10%, more preferably at least 15%, and even more preferably 25% or more. Ideally, the present compositions would reduce or inhibit microbial activity by at least 1-log reduction.

Bio-compatible is intended to mean that the present compositions do not adversely affect a human being or an animal in contact with a medical device comprising the monomers of formula (I). Such bio-compatibility can be considered to be measured by the parameters of clinical success in the particular use for which the present compositions are put. Clinical success for a given application is understood in the art.

The monomers of the present invention are silicone-containing monomers comprising a silicone-containing moiety and an oxazolidinone moiety of Formula (I). The oxazolidinone moiety may be incorporated into or grafted onto a silicone containing compound.

The present invention is directed to a silicone-containing monomer of formula (I);

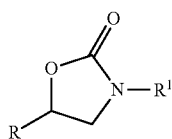

(I)

wherein said silicone-containing monomer comprises a silicone-containing moiety and an oxazolidinone moiety; and wherein R is a silicone-containing moiety, and $R^1$ may be an H,

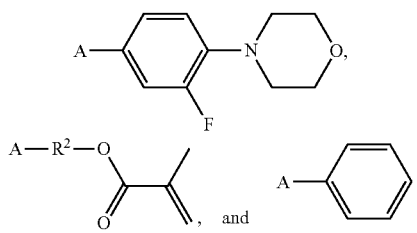

wherein A represents the oxazolidinone ring of the oxazolidinone moiety and $R^2$ is a divalent $C_{1-2}$ alkylene or a $C_6$-$C_{30}$ arylalkylene radical with the proviso that $R^1$ is not a halogen atom.

By oxazolidinone-containing moiety is meant structures comprising the below structural element:

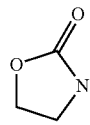

The silicone-containing monomer may contain polymerizable groups, which can bond to reactive mixture components during processing or may be devoid of polymerizable groups. Preferred polymerizable silicone-containing monomers of formula (I) have at feast one ethylenically unsaturated group that allows covalent incorporation of the silicone-containing monomers into the lens matrix or onto the lens surface. Suitable ethylenically unsaturated groups include methacrylates, acrylates, styrenes, mixtures thereof or the like. The ethylenically unsaturated groups may be directly linked to the silicone-containing monomer or may include intervening branched or unbranched alkyl chains, substituted or unsubstituted aryl groups, polyethers, polyamides, polyesters and the like. Silicone-containing monomers which are devoid of polymerizable groups become entangled within the lens material (and therefore be linked to the silicone hydrogel material) when the silicone containing monomer is polymerized, forming a semi-interpenetrating network.

Suitable silicone-containing moieties R may include those of the formula

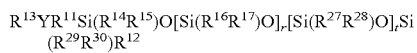

in which:
$R^{14}$, $R^{15}$, $R^{16}$, $R^{17}$, $R^{27}$, $R^{28}$, $R^{29}$, and $R^{30}$, independently of one another, are $C_{1-8}$ alkyl, $C_{1-4}$ alkyl-substituted phenyl, $C_{1-4}$ alkoxy-substituted phenyl, fluoro($C_{1-18}$ alkyl), cyano($C_{1-12}$ alkyl), hydroxy-$C_{1-6}$ alkyl, amino-$C_{1-6}$ alkyl;

Y denotes —COO—, —CONR$^{18}$—, —OCOO—, or —OCONR$^{18}$—, where each $R^{18}$ is independently H or $C_{1-7}$ alkyl;

$R^{11}$ denotes a divalent $C_{1-25}$ alkylene or $C_{6-30}$ arylalkylene radical, which may be interrupted by —O—, —COO—, —CONR$^{18}$—, —OCOO— or —OCONR$^{18}$— and may comprise a hydroxy group, a primary, secondary, or tertiary amine group, a carboxy group, or carboxylic acid;

$R^{12}$ is a monovalent $C_{1-25}$ alkyl or $C_{6-30}$ aryl radical, which may be interrupted by —O—, —COO—, —CONR$^{14}$—, —OCOO— or —OCONR$^{14}$— and may comprise a hydroxy group, a primary, secondary, or tertiary amine group, or a carboxy group;

$R^{13}$ is a monovalent $C_{1-25}$ alkyl or $C_{6-30}$ aryl radical, which comprises at least one hydroxy group, primary or secondary amine group, carboxy group, or site of olefinic unsaturation; and r and t independently of each other are an integer of up to 700 and (r+t) is from 5 to 700.

The silicone-containing moiety R is preferably a siloxane, and may have the general structure of:

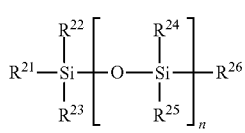

(II)

wherein $R^{21}$ is a monovalent $C_{1-25}$ alkyl or $C_{6-30}$ aryl radical, which may interrupted by —O—, —COO—, —CONR$^{14}$—, —OCOO— or —OCONR$^{14}$— and may comprise a hydroxy group, a primary, secondary, or tertiary amine group, or a carboxy group;

$R^{26}$ is a monovalent $C_{1-25}$ alkyl or $C_{6-30}$ awl radical, which comprises at least one hydroxy group, primary or secondary amine group, carboxy group, or site of olefinic unsaturation; and R22 through R25 are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group, $R^{22}$ through $R^{25}$ are preferably hydrogen or alkyl ethers and wherein n ranges from 1-700, or preferably 5-700, or more preferably 5-100, or most preferably 5-50

A silicone-containing moiety may include polymerizable groups. Polymerizable groups may include ethylenically unsaturated groups, as discussed above.

The silicone-containing moiety may have a weight average molecular weight of from 1000 to 1,500,000 Daltons.

Representative examples of alkyl groups far use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, and the like.

Representative examples of fluoroalkyl groups for use herein include, by way of example, a straight or branched alkyl group as defined above having one or more fluorine atoms attached to the carbon atom, e.g., $-CF_3$, $-CF_2CF_3$, $-CH_2CF_3$, $-CH_2CF_2H$, $-CF_2H$ and the like.

Representative examples of ester groups for use herein include, by way of example, a carboxylic acid ester having 1 to 20 carbon atoms and the like.

Representative examples of ether or polyether containing groups for use herein include, by way of example, an alkyl ether, cycloalkyl ether, cycloalkenyl ether, aryl ether, arylalkyl ether wherein the alkyl, cycloalkyl, cycloalkylalkyl, cycloalkenyl, aryl, and arylalkyl groups are defined above, e.g., alkylene oxides, poly(alkylene oxide)s such as ethylene oxide, propylene oxide, butylene oxide, poly(ethylene oxide)s, poly(ethylene glycol)s, poly(propylene oxide)s, polybutylene oxide)s and mixtures or copolymers thereof, an ether or polyether group of the general formula $-R^7OR^8$, wherein $R^7$ is a bond, an alkyl, cycloalkyl or aryl group as defined above and $R^8$ is an alkyl, cycloalkyl or aryl group as defined above, e.g., $-CH_2CH_2OC_8H_5$ and $-CH_2CH_2OC_2H_5$, and the like.

Representative examples of amide groups for use herein include, by way of example, an amide of the general formula $R^9C(O)NR^{10}R^{31}$ wherein $R^9$, $R^{10}$ and $R^{31}$ are independently $C_1$-$C_{30}$ hydrocarbons, e.g., $R^9$ can be alkylene groups, arylene groups, cycloalkylene groups and $R^{10}$ and $R^{31}$ can be alkyl groups, aryl groups, and cycloalkyl groups as defined herein and the like.

Representative examples of amine groups for use herein include, by way of example, an amine of the general formula $-R^{32}NR^{33}R^{34}$ wherein $R^{32}$ is a $C_2$-$C_{30}$ alkylene, arylene, or cycloalkylene and $R^{33}$ and $R^{34}$ are independently $C_1$-$C_{30}$ hydrocarbons such as, for example, alkyl groups, aryl groups, or cycloalkyl groups as defined herein, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of alkoxy groups for use herein include, by way of example, an alkyl group as defined above attached via oxygen linkage to the rest of the molecule, i.e., of the general formula $-OR^{16}$, wherein $R^{35}$ is an alkyl, cycloalkyl, cycloalkenyl, aryl or an arylalkyl as defined above, e.g., $-OCH_3$, $-OC_2H_5$, or $-OC_6H_5$, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronaphthyl, adamantyl and norbornyl groups bridged cyclic group or spirobicyclic groups, e.g., sprio-(4,4)-non-2-yl and the like, optionally containing one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronaphthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., $-CH_2C_8H_5$, $-C_2H_5C_6H_5$ and the like, wherein the aryl group can optionally contain one or more heteroatoms, e.g., O and N, and the like.

Representative examples of fluoroaryl groups for use herein include, by way of example, an aryl group as defined above having one or more fluorine atoms attached to the aryl group.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spire ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic).

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocylic ring radical as defined above. The heterocyclic, ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined above directly bonded to an alkyl group as defined above. The heterocycloalkyl radical may be attached to the main structure at the carbon atom in the alkyl group that results in the creation of a stable structure.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring', 'substituted heteroarylalkyl', 'substituted heterocycloalkyl ring', 'substituted cyclic ring' and 'substituted carboxylic acid derivative' may be the same or different and include one or more substituents such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, aryl, substituted or unsubstituted heteroaryl, 'substituted heterocycloalkyl ring' substituted or unsubstituted heteroarylalkyl, or a substituted or unsubstituted heterocyclic ring.

Preferred monomers are selected from the group consisting of:

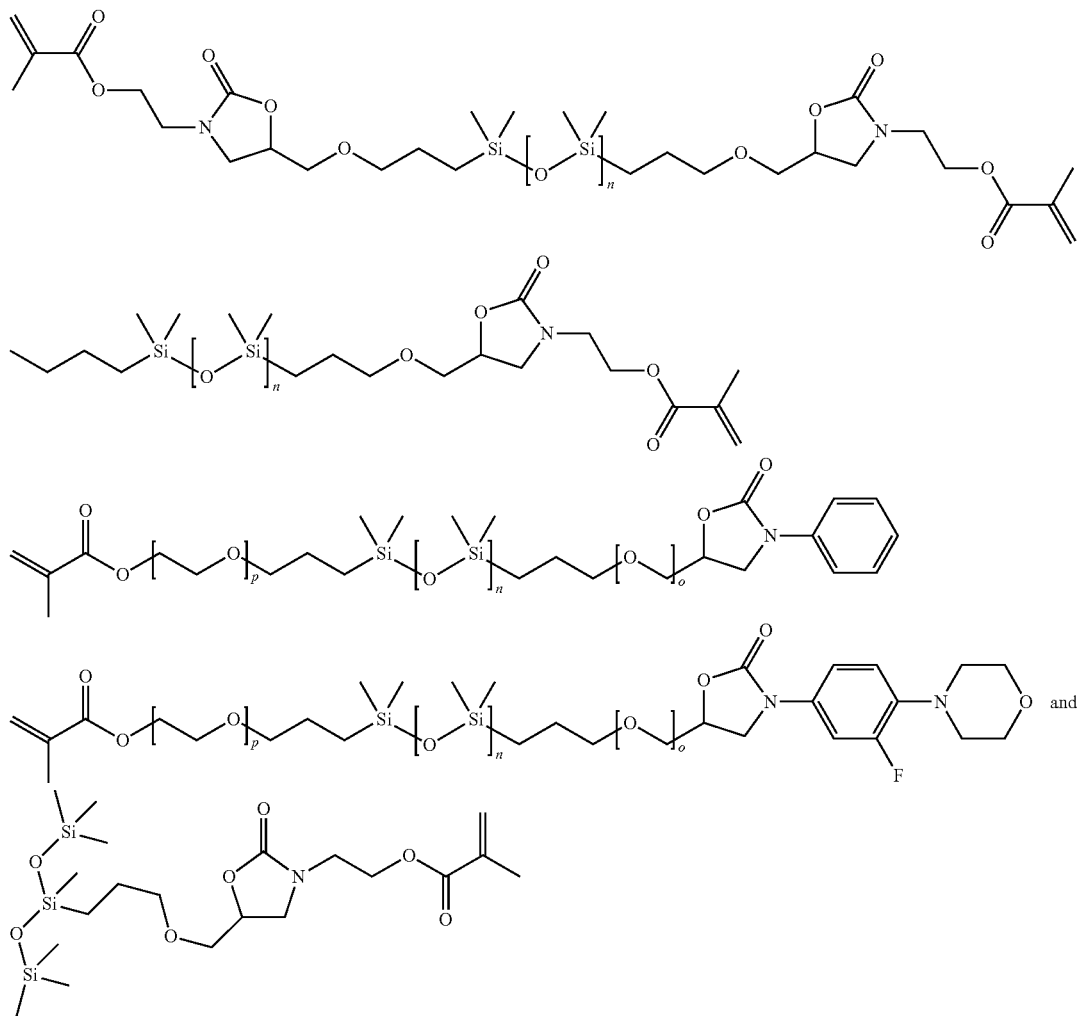

substituted heterocycloalkyl ring, substituted or unsubstituted heteroarylalkyl, substituted or unsubstituted heterocyclic ring, substituted or unsubstituted guanidine, —COORx, —C(O)Rx, —C(S)Rx, —C(O)NRxRy, —C(O)ONRxRy, —NRxCONRyRz, —N(Rx)SORy, —N(Rx)SO2Ry, -(.dbd.N—N(Rx)Ry), —NRxC(O)ORy, —NRxRy, —NRxC(O)Ry-, —NRxC(S)Ry-NRxC(S)NRyRz, —SONRxRy-, —SO2NRxRy-, —ORx, —ORxC(O)NRyRz, —ORxC(O)ORy-, —OC(O)Rx, —OC(O)NRxRy, —RxNRyC(O)Rz, —RxORy, —RxC(O)ORy, —RxC(O)NRyRz, —RxC(O)Rx, —RxOC(O)Ry, —SRx, —SORx, —SO₂Rx, —ONO₂, wherein Rx, Ry and Rz in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted wherein n is an integer ranging from 1-700, o is an integer ranging from 0 to 1, and p is an integer ranging from 0-50.

A composition according to the invention comprises a silicone-containing monomer of formula (I) and et least one other monomer.

The composition preferably comprises 1-90 wt %, based on the total weight of the composition, of a silicone-containing monomer; more preferably 1-50 wt %, most preferably 10-50 wt %.

The composition preferably comprises 10-99 wt % based on the total weight of the composition of a least one other monomer, more preferably 50-99 wt %, most preferably 50-90 wt %.

The present compositions can include antimicrobial metal salts. As used herein, the term "metal salt" means any molecule having the general formula of one or more positively charged metals and one or more negatively charged ions. The metal may be any positively charged metal ion selected from, but not limited to, the following $Al^{+3}$, $Cr^{+2}$, $Cr^{+3}$, $Cd^{+1}$, $Cd^{+2}$, $Co^{+2}, Co^{+3}, Ca^{+2}, Mg^{+2}, Ni^{+2}, Ti^{+2}, Ti^{+3}, Ti^{+4}, V^{+2}, V^{+3}, V^{+5}, Sr^{+2}, Fe^{+2}, Fe^{+3}, Au^{+2}, Au^{+3}, Au^{+1}, Ag^{+2}, Ag^{+1}, Pd^{+2}, Pd^{+1}, Pt^{+2}, Pt^{+4}, Cu^{+1}, Cu^{+2}, Mn^{+2} Mn^{+3}, Mn^{+4}, Zn^{+2}, Se^{+4}, Se^{+2}$ and mixtures thereof. Examples of X include but are not limited to $CO_3^{-2}, NO_3^{-1}, PO_4^{-3}, Cl^{-1}, I^{-1}, Br^{-1}, S^{-2}, O^{-2}$, acetate, mixtures thereof and the like. The negatively charged ions include ions containing $CO_3^{-2} SO_4^{-2}, PO_4^{-3}, Cl^{-1}, I^{-1}, Br^{-1}, S^{-2}, O^{-2}$, acetate and the like, such as $C_{1-5}$ alkyl$CO_2^{-1}$. As used herein the term metal salts do not include zeolites, such as those disclosed in US-2003-0043341-A1. In one embodiment 1, 2, or 3 metal ions may be used. In one embodiment there is 1, 2, or 3 negatively charged ions. One useful metal ion is $Ag^{+1}$. Examples of suitable metal salts include but are not limited to manganese sulfide, zinc oxide, zinc carbonate, calcium sulfate, selenium sulfide, copper iodide, copper sulfide, and copper phosphate. Examples of silver salts include but are not limited to silver carbonate, silver phosphate, silver sulfide, silver chloride, silver bromide, silver iodide, and silver oxide. In one embodiment the metal salt comprises at least one silver salt such as silver iodide, silver chloride, and silver bromide.

The compositions of the present invention may be complexed with silver salts. The compositions of the present invention may be post-treated with a silver halide solution during the manufacturing process to thereby produce a desired silver salt.

The compositions of the present invention may also be complexed with a halogen, including iodine or bromine. The amount of iodine or bromine, generally in trace amounts. The complexation may be carried out before curing the composition or contact lens, or after the curing of the contact lens. The composition most preferably comprises a silver salt, bromine or iodine.

The silicone-containing monomers may be incorporated into the selected polymer by a number of methods. For example, a silicone-containing monomer containing compound may be dispersed or dissolved into the monomer and/or prepolymer mixtures (reactive mixtures), which are used to form the ophthalmic device.

Further, the silicone-containing monomers may be used as a compatibillzing component in a silicone hydrogel contact lens formulation. Finely, the present inventive monomers may be used in developing surfaces with antimicrobial properties. These may be on the surfaces of polymers, devices, or polymer-coated devices.

Examples of a hydrophobic component of utility in contact lenses are silicone containing monomers and saturated hydrocarbon compounds. Examples of hydrophilic components include acyclic or cyclic amide-, ester-, urethane-, urea-, and other hetero atom containing linear or oligomeric compounds.

Lenses prepared from a cured composition comprising the silicone-containing monomers of the present invention may be coated with a number of agents that are known in the art to coat lenses such as by the procedures, compositions, and methods of U.S. Pat. Nos. 3,854,982; 3,916,033; 4,920,184; 5,002,794; 5,712,327; and 5,067,415 as well as WO 0127662, the entire contents of which are hereby incorporated by reference. In addition to the cited patents, there are other known methods of treating a lens once ft is formed. The lenses of this invention may be treated by these methods, which are illustrated in U.S. Pat. No. 5,453,467; U.S. Pat. No. 5,422,402; WO 9300391; U.S. Pat. No. 4,973,493; and U.S. Pat. No. 5,350,800 of which the entire contents are hereby expressly incorporated by reference.

In another aspect of the present invention the composition comprising the silicone-containing monomer may be used to coat a silicone containing polymer surface or a SiHy polymer surface. Alternatively, the composition can be used to coat a polymer surface, a device surface, a SiHy polymer surface, a oxazolidinone bearing silicone polymer surface, etc. In such coating process the contact lens is treated with a solution containing the instant silicone-containing monomer of formula (I) followed by polymerization in the presence of suitable radical initiator to yield the said coating. The non-polymerizable silicone monomers of formula (I) will also find utility in a lens packaging solution during the manufacturing process of contact lenses to support inclusion of silicones into a contact lens matrix. This can be achieved by agitation, ultra-sonication, or by application of an energy source such as heat, steam, thermal, or other source of radiation. Alternatively, the incorporation of the non-polymerizable silicone monomers of formula (I) of the invention into the contact lens can be achieved during the sterilization step of the manufacturing process of contact lenses.

The present invention includes methods to prepare reactive silicone monomers with surface wettable/lubricious functions and optionally anti-infective components built in to an oxygen permeable silicone moiety.

Oxazolidinones are a promising new class of synthetic antibiotics active against multidrug-resistant Gram-positive bacteria. This oxazolidinone moiety forms the structural components of one of the commercially important class of antibiotics (e.g. Linezolid, Zyvox®) and also has found application as anticoagulants (e.g. Rivaroxaban®). [See http://en.wikipedia.org/wiki/Linezolid; http://en.wikipedia.org/wiki/Zyvox; http://en.wikipedia.org/wiki/Rivaroxaban; Fung et al. Clinical therapeutics 23(3), 2001, 356-391: Diekema and Jones The Lancet, 358, 2001, 1975-1982].

Oxazolidinone based compounds have also been reported in the use of topical antibiotic compositions for treating eye infections. [See US20020107238 A1] The introduction of oxazolidinone moieties into silicones provides the beneficial properties of wettability, compatibility with both hydrophilic and hydrophobic components of a hydrogel formulation as well as the potential of providing a disinfecting surface on the final device.

The synthesis of the silicone monomers takes advantage of cyclization chemistries of isocyanates with oxiranes and other cyclic compounds capable of forming hydrophilic 5 membered cyclic oxazolidinone ring. One example is the generation of an silicone-containing monomer built in to the silicone monomer. Other examples include adding an silicone-containing monomer to the end of the monomer.

Oxazolidinone bearing silicones can be prepared from a variety of commercially available oxirane functionalized silicones by cyclization reaction with suitable isocyanates, leading to efficient manufacture. A process for the preparation of a silicone-containing monomer of formula (I), comprises providing an oxirane-functionalized silicone-containing moiety R and react this oxirane-functionalized silicone-containing moiety R with an isocyanate-functionalized group $R^1$. The isocyanate-functionalized compound $R^1$ preferably also comprises a (meth)acrylate group.

Scheme 1: Synthesis of difunctional silicone-containing monomer

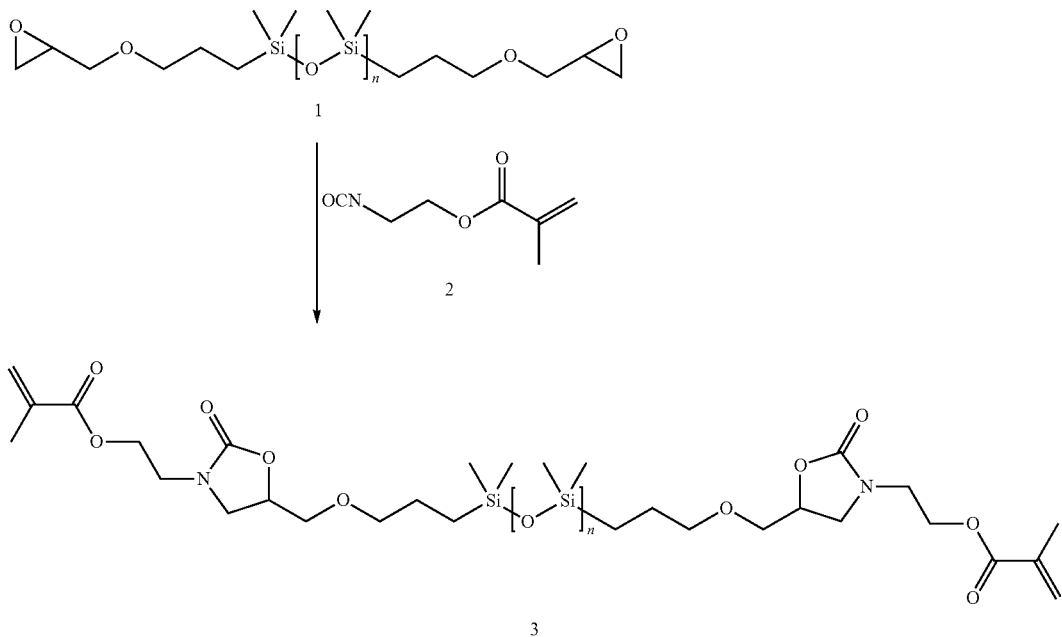

Synthesis of a difunctional silicone monomer is exemplified in Scheme 1. Alternatively, the disclosed products and its derivatives can be accessed via reaction between diisocyanato silicones and allyl glycidyl ether.

In scheme 1, n is an integer ranging from 1-700, or preferably 5-700, or more preferably 5-100, or most preferably 5-50.

Synthesis of a monofunctional silicone-containing monomer is shown in Scheme 2.

In scheme 2, n is an integer ranging from 1-700, or preferably 5-700, or more preferably 5-100, or most preferably 5-50.

Synthesis of reactive monofunctional silicone methacrylate compounds with phenyl oxazolidinone end functions, is shown in Scheme 3.

Scheme 2: Synthesis of monofunctional silicone-containing monomer

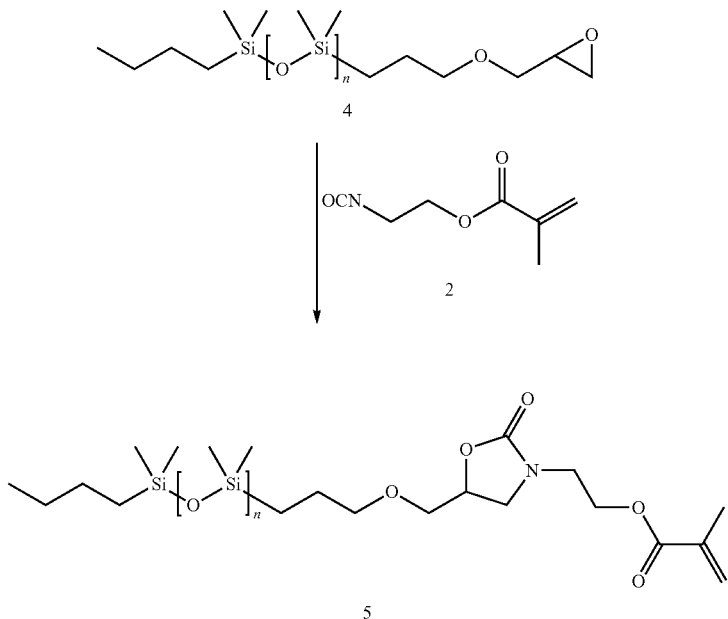

Scheme 3: Synthesis of reactive monofunctional Silicone compounds bearing phenyl oxazolidinone end functions.

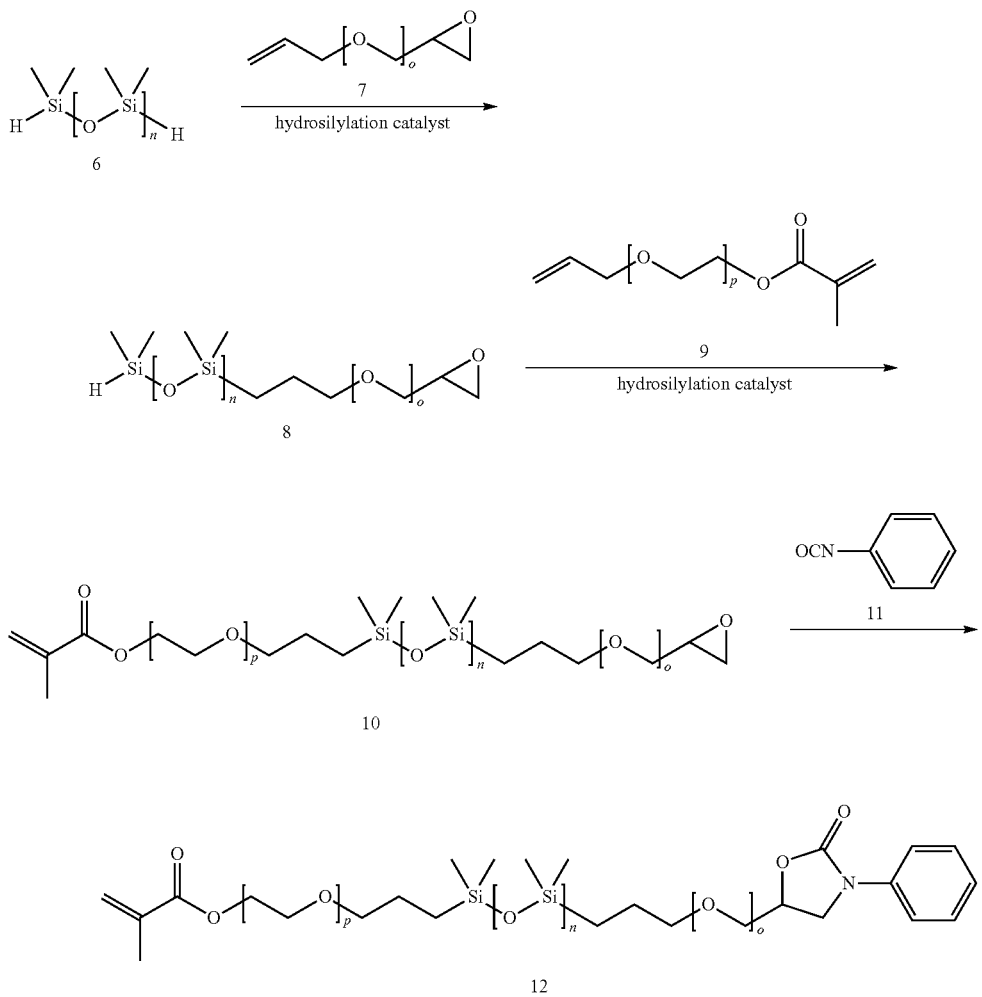

In scheme 3, n is an integer ranging from 1-700, or preferably 5-700, or more preferably 5-100, or most preferably 5-50. o is an integer ranging from 0 to 1 and p is an integer ranging from 0-50.

Synthesis of methacrylated silicone monomers containing oxazolidinone structural features (present in the well known antibiotic—Linezolid)—is illustrated in Scheme 4.

These antibiotics can be accessed from reaction between oxirane(epoxide) derivatives and isocyanate derivatives in a way that has been reported in literature. (See Xingxian at al., J, of Chemical Research 12, 2009, 739-740; Xingxian, Faming Shenqing Gonkai Shuomingshu 2010, CN 1010638392A, 20100203; Heggelund and Undheim, WO 2006074982 A2; Qiang et al., Faming Shenqing Gonkai Shuomingshu 2006, CN 1772750 A, 20060517; Hua at al, Jingxi Huagong 21(1), 2004, 70-71, 75; Perrault and Gadwood WO 2002032857)

Scheme 4: Synthesis of reactive monofunctional silicone-containing monomer

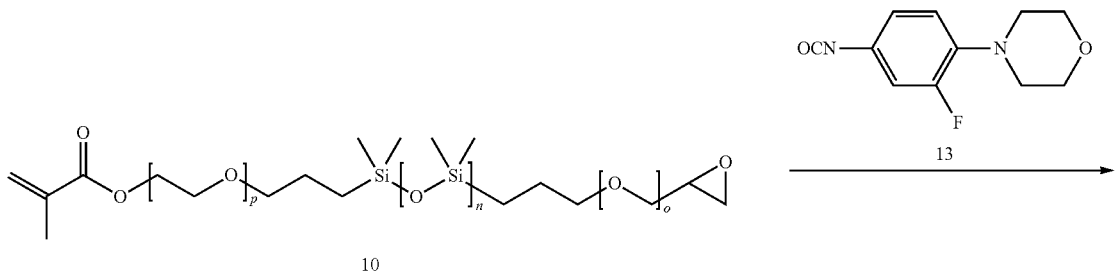

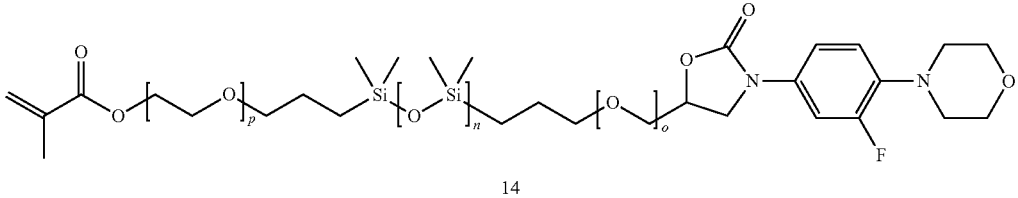

14

In Scheme 4, variables n, o, and p, may have the same values as shown in Scheme 3.

Bacterial resistance of polymeric compositions containing oxazolidinones can be further enhanced by metal salts and/or trace amounts of Iodine or bromine without the unintended discoloration that is possible with similar polyvinylpyrolidonone-iodine systems (see U.S. Pat. No. 3,322,712). The complexation with iodine or bromine may be carried out either before curing the contact lens composition or more preferably by post treating the contact lens with a solution containing required levels of bromine or Iodine to impart bactericidal properties.

Poly(N-vinyl oxazolidinones) are known to complex with silver salts (see U.S. Pat. No. 3,050,028 and U.S. Pat. No. 3,218,169). Compositions containing silicone containing monomers in the presence of silver salts, can be polymerized to generate lenses with inherent broad spectrum antimicrobial properties as a result of Inclusion of complexed silver in the lenses. Alternatively, contact lenses that contain a polymerized oxazolidinone monomer may be post treated with silver halide solution during the manufacturing process to generate antimicrobial contact lenses.

The present inventive monomers may be used alone or in mixtures with other monomers to form polymers. Polymers made of the present monomers may be used in mixture with other polymers, or as a composite material, or as a coating or treatment for other polymers.

A method of making articles comprising monomers of the invention herein comprises providing a monomer mixture comprising the silicone-containing monomer of formula (I) and at least one other monomer and subjecting the monomer mixture to polymerizing (curing) conditions to provide a polymerized device. The other monomer preferably comprises a (meth)acrylate group, a (meth)acrylamide group, a vinyl group or an olefinic C—C double bond. Examples of such monomers include are but not limited to methacrylic acid, hydroxyethyl methacrylate, polydimethylsilaxane (PDMS)-methacrylate, allyl methacrylate, dimethylacrylamide, N-vinyl pyrrolidinone, and vinylstyrene.

The monomers are polymerized with each other. During the reaction curing occurs. Typically initiators are needed for curing the specific monomers disclosed in the patent when reacting thermally or by photocuring. However, polymerization can also be effected solely by high energy radiation, for example gamma source or E-beam techniques. Thermal- and photo-initiator amounts of 0.001-10 wt % may be included in the composition. Solvent levels of 0%-80% may be included in the composition. Alcohols are typically used as solvents, but the composition may also include water, aprotic solvents such as DMF, DMSO, diglyme, THF and methylTHF.

The methods may further optionally include treating the device with compatibilizing agents, salts, or coatings, extracting the polymerized device, and packaging and sterilizing the polymerized device. Of course the methods of making devices comprising the claimed compositions are not limited to the above steps.

EXAMPLES

Example 1

Synthesis of Oxazolidinone Containing Silicone Methacrylate

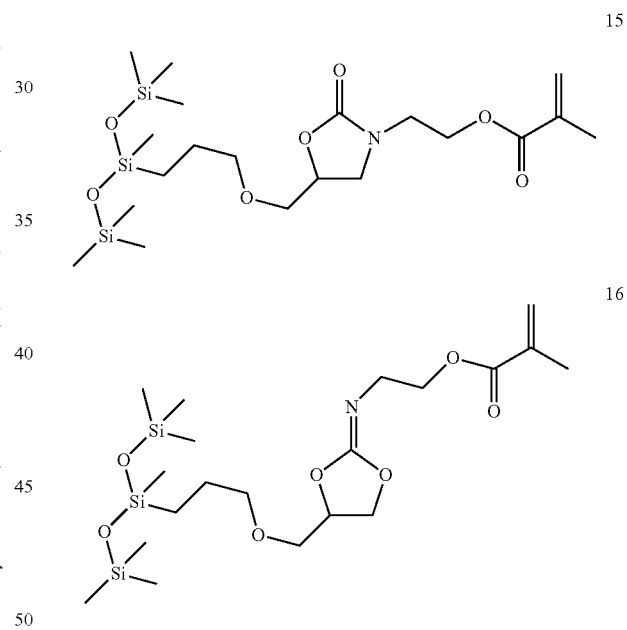

FIG. 3. Structures of Oxazolidinone Containing Silicone Monomers

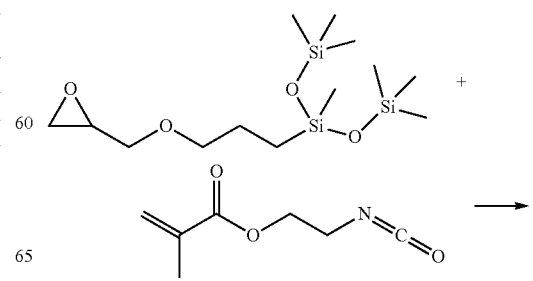

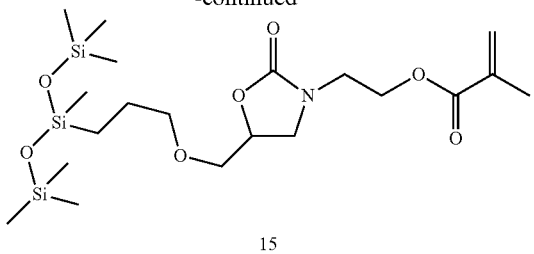

15

The reaction takes place according to the reaction scheme above.

The use of an n-tributyltiniodide-triphenyl phosphine oxide (nBu₃SnI-Ph₃PO) catalyst system facilitated the reaction of the silicone epoxide [3-(glycidoxypropyl) heptamethyltrisiloxane] with isocyanate [2-isocyanatoethyl moth acrylate, IEM] to achieve the target product 15 through the intermediary of 16. The product was characterized by FTIR and $^1$H NMR.

Example 2

Synthesis of Oxazolidinone Containing Silicone Monomers with LiCl Catalyst (a) High temperature reaction: Anhydrous 3-(glycidoxypropyl) heptamethyltrisiloxane (17.66 g, 0.0525 moles), LiCl (1.25 g), and anhydrous DMF (32.35 g) are taken in a round bottom flask (RBF) equipped with magnetic stir bar and set in a high temperature oil bath on a hot plate with stirrer. The RBF was also equipped with a condenser connected to a chiller, nitrogen inlet/outlet and addition funnel. The solution was heated to 155° C. (reflux conditions) at which point 7.76 g (0.05 mmol) IEM was added drop wise to silicone epoxide solution over a period of 1 hour. The clear solution became amber brown colored over the period of addition. FTIR of the sample showed presence of —NCO peak (~2278 cm-1) as well as peak at 1754 cm-1. The reaction was allowed to continue for an additional 3 h, and the FTIR of the reaction mix showed no presence of —NCO peak. The reaction heating was stopped, the reaction mixture allowed to cool to room temperature and gas chromatography (GC) (using in house GC method) performed on the crude. The silicone starting material peak was no longer observed and a peak at higher retention time was assigned to the product (oxazolidinone derivative). Column chromatography (CC) of the crude with varying ratios of Hex:Ethylactetate (8:1 to 1:1) gave the product fraction product 15) Gas chromatography (GC) confirmed the product 15; the purity was 60%

(b) Lower temperature reaction: To overcome the problem of using basic conditions as well as high temperatures a neutral (to only slightly basic) catalyst system and milder temperature conditions were evaluated. For this purpose, tributylphosphine oxide (0.45-4 g, 2.0 mmol) and LiBr (0.129 g, 1.5 mmol) were dissolved in anhydrous toluene (10 g) at roam temperature for 30 minutes to yield a faint (tinted) yellow catalyst solution. This solution was heated to 80° C. and a mixture of anhydrous 3-(glycidoxypropyl) heptamethyltrisiloxane (20.00 g, 59.5 mmol) and 2-isocyanatoethyl methacrylate (9.23 g, 59.5 mmol) dissolved in anhydrous toluene (12.40 g) was added drop wise into this solution over a period of 1.5 hours, FTIR of the reaction mixture 10 minutes after completing the addition of epoxide/isocyanate mixture showed no presence of —NCO band at 2280 cm-1 and a strong band at 1752 cm-1 corresponding to the oxazolidinone. GC of the crude showed no presence of the isocyanate, about 12 area % of the epoxide starting material and 78 area % of the product. The solvent (toluene) was evaporated by Rotovap and the crude product was purified by column chromatography (CC) using 2:1 hexane:ethylacetate solvent mixture. Various fractions were obtained and tested using TLC plate technique for the product. Trace amounts of butylated hydroxytoluene (BHT) were dissolved in the relevant CC fractions and the solvents were evaporated by rotovap. The final product (clear colorless liquid) yield was 78% (22.82 g) and the purity by GC was found to be 98%. The structure of the final product was confirmed by $^1$H NMR to be compound 15.

Example 3

Synthesis of Oxazolidinone Containing Silicone Methacrylate

The low temperature reaction described in example 2b was used to synthesize oxazolidinone containing silicone methacrylate compounds 5-1 and 5-2 as per following scheme:

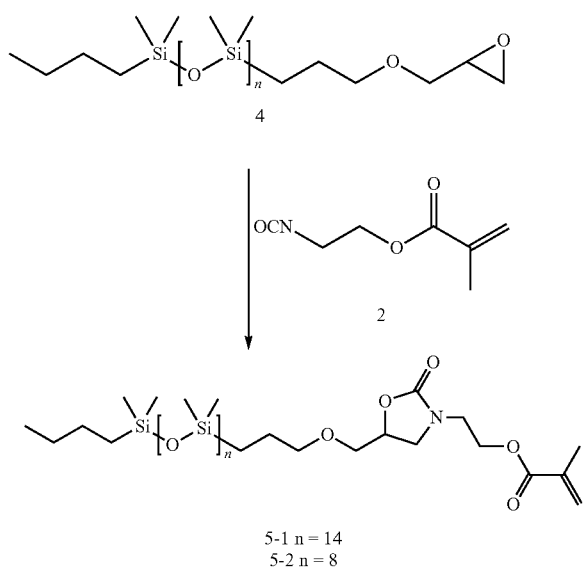

5-1 n = 14
5-2 n = 8

Example 4

Silicone Hydrogel Films Prepared from Formulations Using Compounds 5-2 and 5-2

Formulations were prepared by mixing the silicone containing monomers 5-1 and 5-2 with different reactive monomers. The formulation ingredients and their amounts are given in Table 1. Individual formulation components were weighed into a glass vial, the mixture was sonicated and left at room temperature until a clear homogeneous mixture was formed. The monomer mix was then placed in a polypropylene mold and was cured at 85° C. for 45 min. Isopropyl alcohol (IPA)/H₂O mixtures were used for demolding and for extraction of residual unreacted monomers. The demolded and extracted silicone hydrogel film was subsequently hydrated for 1 hour in water at room temperature to give visually clear and mechanically resilient silicone hydrogel film demonstrating the compatibilizing effect of silicone containing monomers in hydrogel formulations.

When compound 5-1 was replaced with MA-PDMS (Molecular weight 800-1000) which does not contain an oxazolidinone moiety (tabulated in formulation 3), it was found that the monomer mixture was non-homogeneous with two distinct layers indicating phase separation. This demonstrates compatibilizing effect of oxazolidinone containing silicone methacrylate in hydrogel formulations.

TABLE 1

Hydrogel formulations comprising silicone containing monomers

| Components | Formulation 1 wt. (mg) | Formulation 1 wt. % (w/o 1-propanol) | Formulation 2 wt. (mg) | Formulation 2 wt. % | Formulation 3 wt. (mg) | Formulation 3 wt. % |
|---|---|---|---|---|---|---|
| HEMA | 227 | 27 | 225 | 22 | 224 | 22 |
| DMA | 279 | 33 | 283 | 28 | 280 | 28 |
| NVP | 177 | 21 | 187 | 18 | 177 | 18 |
| Compound 5-2 | 141 | 17 | 0 | 0 | 0 | 0 |
| Compound 5-1 | 0 | 0 | 33 | 30 | 0 | 0 |
| MA-PDMS | 0 | 0 | 0 | 0 | 299 | 30 |
| AMA | 10 | 1 | 10 | 1 | 10 | 1 |
| AIBN | 10 | 1 | 10 | 1 | 10 | 1 |
| 1-propanol | 229 | NA | 0.00 | NA | 0.00 | NA |
| Total (w/o 1-propanol) | 843 | NA | 1019 | NA | 1000 | NA |
| Appearance of mixture before curing | Clear homogenous | | Clear homogenous | | Non-homogenous (Phase separated) | |
| Appearance of cured silicone hydrogel | clear | | clear | | N/A | |

HEMA = 2-hydroxyethyl methacrylate;
DMA = dimethyl acrylamide;
NVP = N-vinyl pyrrolidinone;
AMA = allylmethacrylate;
AIBN = azobisisobutyronitrile;
MA-PDMS = Monomethacryloxypropyl terminated polydlmethylsiloxcanes;
NA = Not Applicable The oxazolidinone bearing silicone composition of the present invention can be used to prepare ophthalmic devices, including contact lenses For contact lens applications in accordance with the present invention, the monomer mixtures employed will include a polymerizable materiel of this invention mixed with various conventional lens-forming monomers and compounds. All the lens-forming monomers will normally be monomers that are polymerizable by free radical polymerization, usually an activated unsaturated radical, and most preferably an ethylenically unsaturated (vinyl) radical. The conventional lens-forming monomers may be low molecular weight compounds that are polymerizable by free radical polymerization, or may be higher molecular weight compounds also referred to as prepolymers or macromonomers. Optionally, the initial monomeric mixture may also include additional materials such as solvents, colorants, toughening agents, UV-absorbing agents, and other materials known in the contact lens ail. Representative solvents are disclosed in U.S. Pat. No. 5,260,000 (Nandu et al.) and U.S. Pat. No. 6,020,445 (Vanderlean et al.).

The instant polymers can be readily cured to cast shapes by conventional free radical polymerization methods, where the monomeric mixture is exposed to light radiation, such as visible light or UV radiation, to heat, or to both, in order to induce polymerization. Representative free radical thermal polymerization initiators are organic peroxides, such as acetal peroxide, lauroyl peroxide, decanoyl peroxide, stearoyl peroxide, benzoyl peroxide, tert-butyl peroxypivalate, peroxydicarbonate, and the like, employed in a concentration of about 0.01 to 1 percent by weight of the total monomer mixture. Representative UV initiators are those known in the field such as, benzoin methyl ether and benzoin ethyl ether.

Persons skilled in the art are well aware of how to make silicone hydrogel contact lenses in general. See, e.g., U.S. Pat. No. 4,600,571 (Lee et al.); U.S. Pat. No. 7,268,198 (Kunzler et al); and U.S. Pat. No. 7,540,609 B2 (Chen et el.), the entire contents of which are hereby incorporated by reference.

Based upon the present disclosure, persons skilled in the art will readily understand how to make silicone hydrogel contact lenses incorporating the novel silicone containing monomers disclosed herein.

Specific exemplary embodiments of the present invention have been shown and described in the foregoing specification. It will be appreciated by those skilled in the art, however, that variations may be made to the illustrative embodiments without departing from the principles and spirit of the present invention.

The invention claimed is:

1. A silicone-containing monomer of formula (I);

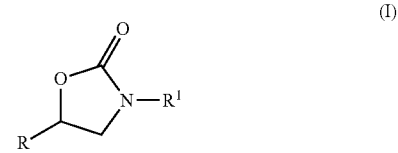

wherein said silicone-containing monomer comprises a silicone-containing moiety and an oxazolidinone moiety and wherein R is a silicone-containing moiety, and $R^1$ is a moiety selected from the group consisting of

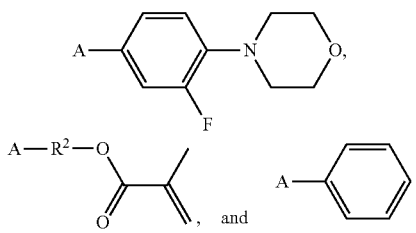, and 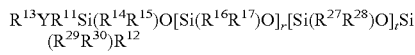

wherein A represents the oxazolidinone ring of the oxazolidinone moiety and $R^2$ is a divalent $C_{1-25}$ alkylene or a $C_{6-30}$ arylalkylene.

2. The monomer of claim 1, wherein the silicone-containing moiety R has the formula:

$$R^{13}YR^{11}Si(R^{14}R^{15})O[Si(R^{16}R^{17})O]_r[Si(R^{27}R^{28})O]_tSi(R^{29}R^{30})R^{12}$$

in which:
$R^{14}, R^{15}, R^{16}, R^{17}, R^{27}, R^{28}, R^{29}$, and $R^{30}$, independently of one another, are $C_{1-8}$ alkyl, $C_{1-4}$ alkyl-substituted phenyl, $C_{1-4}$ alkoxy-substituted phenyl, fluoro($C_{1-18}$ alkyl), cyano($C_{1-12}$ alkyl), hydroxy-$C_{1-6}$ alkyl, or amino-$C_{1-6}$ alkyl;

Y denotes —COO—, —CONR$^{18}$—, —OCCO—, or —OCONR$^{18}$—, where each $R^{18}$ is independently H or $C_{1-7}$ alkyl;

$R^{11}$ denotes a divalent $C_{1-25}$ alkylene or $C_{6-30}$ arylalkylene radical, which may interrupted by —O—, —COO—, —CONR$^{18}$—, —OCOO— or —OCONR$^{18}$— and may comprise a hydroxy group, a primary, secondary, or tertiary amine group, a carboxy group, or carboxylic acid;

$R^{12}$ is a monovalent $C_{1-25}$ alkyl or $C_{6-30}$ aryl radical, which may interrupted by —O—, —COO—, —CONR$^{14}$—, —OCOO— or —OCONR$^{14}$— and may comprise a hydroxy group, a primary, secondary, or tertiary amine group, or a carboxy group;

$R^{13}$ is a monovalent $C_{1-25}$ alkyl or $C_{6-30}$ aryl radical, which comprises at least one hydroxy group, primary or secondary amine group, carboxy group, or site of olefinic unsaturation;
and r and t independently of each other are an integer of up to 700 and (r+t) is from 1 to 700.

3. The monomer of claim 1, wherein the silicone containing moiety R has the formula

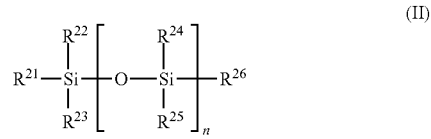

wherein
$R^{21}$ is a monovalent $C_{1-25}$ alkyl or $C_{6-30}$ aryl radical, which may interrupted by —O—, —COO—, —CONR$^{14}$—, —OCOO— or —OCONR$^{14}$— and may comprise a hydroxy group, a primary, secondary, or tertiary amine group, or a carboxy group;

$R^{26}$ is a monovalent $C_{1-25}$ alkyl or $C_{6-30}$ awl radical, which comprises at least one hydroxy group, primary or secondary amine group, carboxy group, or site of olefinic unsaturation;

$R^{22}$ through $R^{25}$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group and n ranges from 1-700.

4. The monomer of claim 1, wherein the monomer is selected from the group consisting of:

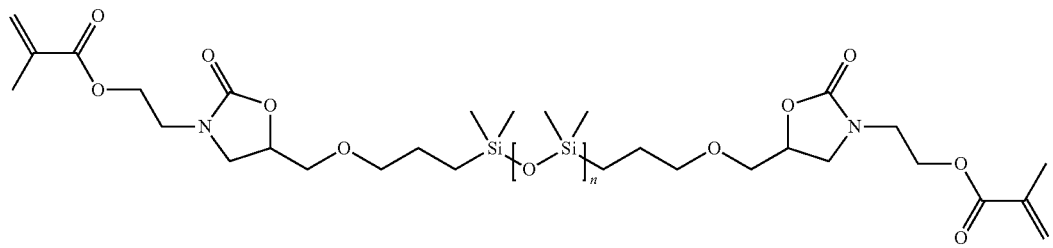

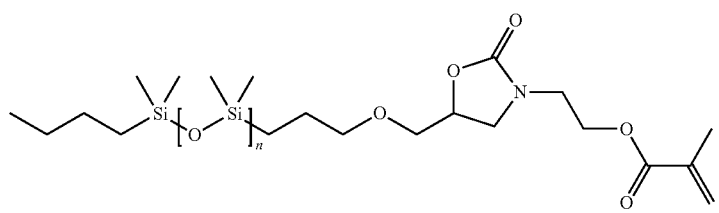

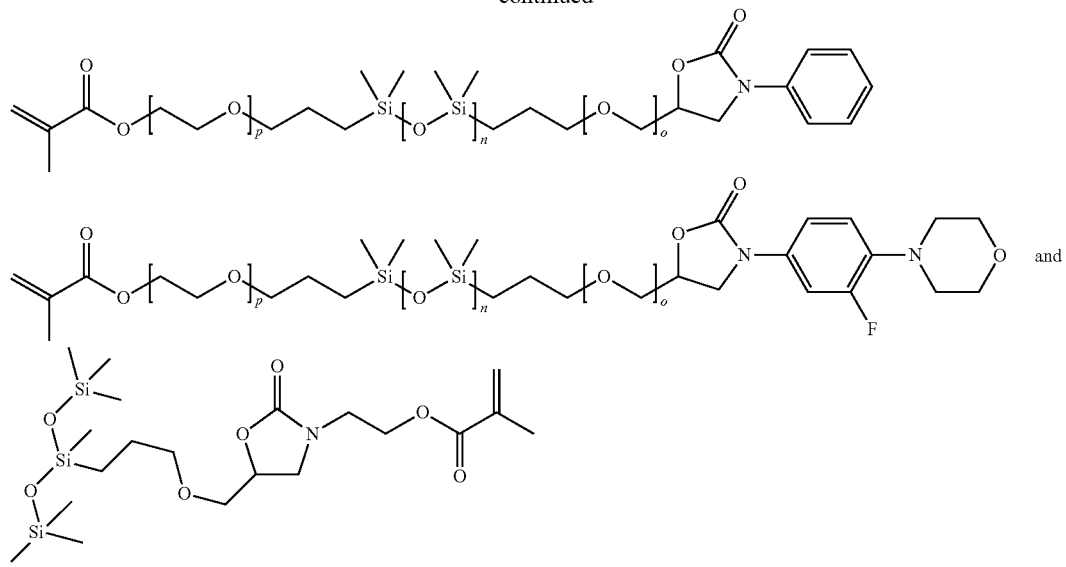

wherein n is an integer ranging from 1-700, o is an integer ranging from 0 to 1, and p is an integer ranging from 0-50.

5. Composition comprising a silicone-containing monomer according to any one of claims 1-4 and at one other monomer.

6. The composition of claim 5, complexed with bromine or iodine.

7. Composition according to claim 5, comprising 1-90 wt % based on the total weight Of the composition of said silicone-containing monomer.

8. Composition according to claim 5, comprising 10-99 wt % based on the total weight of the composition of said at least one other monomer.

9. The composition of claim 5, further comprising a silver salt.

10. Composition of claim 5, further comprising an initiator and the composition is thermally cured or cured by ultraviolet radiation.

11. A medical device comprising the cured composition of claim 10.

12. The medical device of claim 11, wherein the device is an ophthalmic device.

13. The medical device of claim 11, wherein the device is a contact lens.

14. A process for the preparation of a silicone-containing monomer according to claim 1, comprising providing an oxirane-functionalized silicone-containing moiety R according to claim 1 and react this oxirane-functionalized silicone-containing moiety R with an isocyanate-functionalized group $R^1$ according to claim 1.

15. A process according to claim 14, wherein the isocyanate-functionalized compound $R^1$ also comprises a (meth)acrylate group.

* * * * *

UNITED STATES PATENT AND TRADEMARK OFFICE
CERTIFICATE OF CORRECTION

| | | Page 1 of 1 |
|---|---|---|
| PATENT NO. | : 9,086,527 B2 | |
| APPLICATION NO. | : 14/109951 | |
| DATED | : July 21, 2015 | |
| INVENTOR(S) | : James Parakka et al. | |

It is certified that error appears in the above-identified patent and that said Letters Patent is hereby corrected as shown below:

In the Claims

In column 25:

In lines 17 and 18, delete the structural formula and replace it with the following structural formula:

-- $R^{13}YR^{11}Si(R^{14}R^{15})O[Si(R^{16}R^{17})O]_r[Si(R^{27}R^{28})O]_tSi(R^{29}R^{30})R^{12}-$ --.

Delete the entire text in line 35 and replace it with the following text:

-- $R^{12}$ is a $C_{1-25}$ alkylene or $C_{6-30}$ arylene radical linked to the oxazolidinone moiety, which --.

In column 26:

In lines 6-13, delete the structural formula and replace it with the following structural formula:

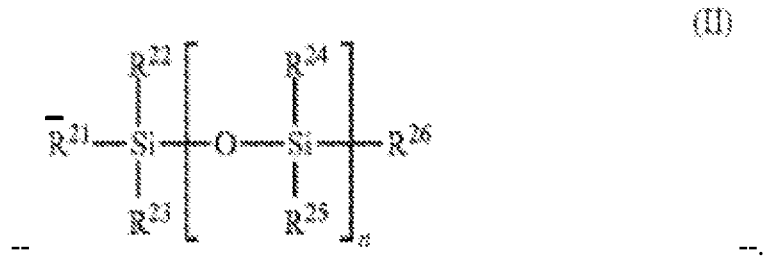

Delete the entire text in line 14 and replace it with the following text:

-- $R^{21}$ is a $C_{1-25}$ alkylene or $C_{6-30}$ arylene radical linked to the oxazolidinone moiety, which --.

Delete the entire text in line 19 and replace it with the following text:

-- $R^{26}$ is a monovalent $C_{1-25}$ alkyl or $C_{6-30}$ aryl radical linked to the oxazolidone moiety, which --.

Signed and Sealed this
Ninth Day of August, 2016

Michelle K. Lee
*Director of the United States Patent and Trademark Office*